United States Patent [19]

Haenni et al.

[11] 4,169,103

[45] Sep. 25, 1979

[54] NONATETRAENOIC ACID DERIVATIVES

[75] Inventors: Ralph Haenni, Fullinsdorf; Gottlieb Ryser, Basel, both of Switzerland

[73] Assignee: Hoffmann-La Roche Inc., Nutley, N.J.,

[21] Appl. No.: 895,942

[22] Filed: Apr. 12, 1978

[51] Int. Cl.$^2$ ............................ C11C 1/00; C11C 3/02
[52] U.S. Cl. .......................... 260/413; 260/410.9 V; 424/312; 424/318
[58] Field of Search ............ 260/413 L, 413 K, 413 R

[56] References Cited

PUBLICATIONS

Rao, M. et al., Chem. Absts., vol. 77, No. 164875e (1972).
Barua, A. et al., Chem. Absts., vol. 77, No. 34726w (1972).
Rietz, et al., Vitamins and Hormones, vol. 32, pp. 237-249 (1974).

*Primary Examiner*—John F. Niebling
*Attorney, Agent, or Firm*—Jon S. Saxe; Bernard S. Leon; William H. Epstein

[57] ABSTRACT

The compound 9-(2,2,5-trimethyl-4-hydroxy or oxo-1-cyclohexenyl)-3,7-dimethyl-2,4,6,8-nonatetraenoic acid and derivatives useful as antitumor agents and in the prophylaxis and/or treatment of certain carcinomas.

1 Claim, No Drawings

NONATETRAENOIC ACID DERIVATIVES

SUMMARY OF THE INVENTION

In accordance with this invention, it has been found that compounds of the formula

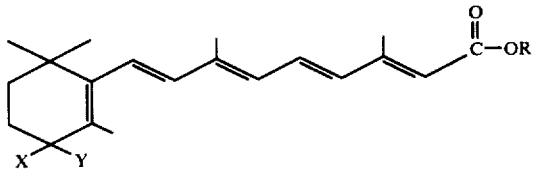

wherein R is hydrogen, or lower alkyl; X is individually hydrogen, Y is individually hydroxy or X and Y taken together form oxo and pharmaceutically acceptable salts thereof; are useful as anti-tumor agents.

In accordance with the present invention, a prophylaxis against certain premalignant and carcinomic conditions in mammals is afforded through the systemic administration of an effective amount of the compound of formula I or its pharmaceutically acceptable salts.

In accordance with another embodiment of this invention, there is provided a method for the therapeutic treatment in mammals of carcinomas, particularly of the skin, gastrointestinal tract, respiratory tract, genito-urinary tract, mammary glands and bladder by the systemic administration of the compound of formula I and/or its pharmaceutically acceptable salts.

DETAILED DESCRIPTION

As used herein, the term "halogen" includes all four halogens, i.e., chlorine, bromine, fluorine and iodine. The term "lower alkyl" designates lower alkyl groups containing from 1 to 7 carbon atoms such as methyl, ethyl, propyl, isopropyl, etc.

As used herein, the term "aryl" designates aromatic hydrocarbon radicals containing from 6 to 20 carbon atoms such as phenyl or mono or poly-lower alkyl substituted phenyl radicals such as tolyl.

In accordance with this invention, the compound of formula I where R is lower alkyl and X and Y form oxo, i.e., a compound of the formula

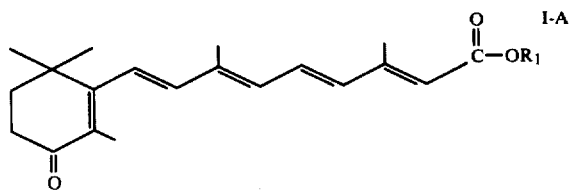

where $R_1$ is lower alkyl is prepared by reacting a compound of the formula:

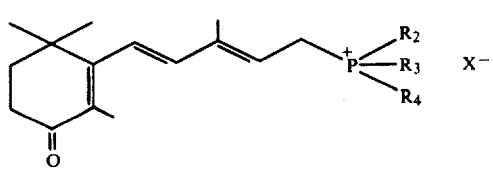

wherein X is halogen; and $R_2$, $R_3$ and $R_4$ are phenyl, with a

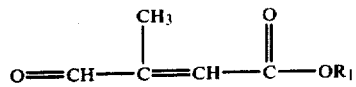

wherein R is as above via a Wittig reaction utilizing conditions conventional in Wittig reactions.

The compound of formula I-A can be hydrolyzed by reaction with an inorganic base such as sodium hydroxide to produce the compound of formula I wherein X and Y are oxo and R is hydrogen, i.e. a compound of the formula:

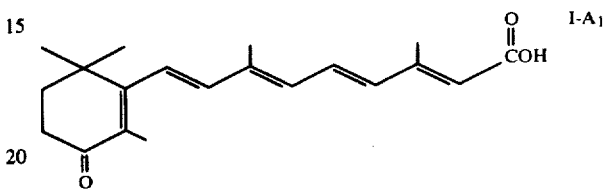

Any conventional method of inorganic basic hydrolysis can be utilized to convert the compound of formula I-A to the compound I-A$_1$.

Both the compounds of formula I-A and I-A$_1$ can be converted by reduction with an alkali metal borohydride to the compound of formula I where Y is hydroxy and X is hydrogen, i.e. a compound of the formula

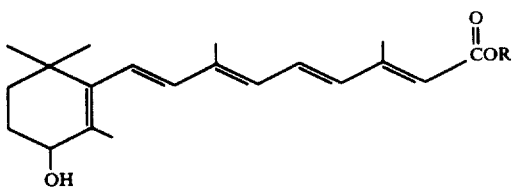

wherein R is as above.

Any conventional method of reducing with an alkali metal borohydride can be utilized to carry out this reaction.

The compounds of formula I are effective in mammals in reducing the growth of tumors such as papillomas and chondrosarcoma. When chondrosarcoma tumors transplanted into rats and the rats were administered either one of the following compounds: Compound A=9-(2,6,6-trimethyl-3-oxo-1-cyclohexen-1-yl)-3,7-dimethyl-2,4,6,8-tetraenoic acid;

Compound B=9-(2,6,6-trimethyl-3-hydroxy-1-cyclohexen-1-yl)-3,7-dimethyl-2,4,6,8-tetraenoic acid, there was substantial inhibition of the growth of this tumor. The compounds A and B when administered to rats by this test over a four week period at dose of 20 mg/kg/day i.p. caused 94% and 95% inhibition respectively without any toxicity. This inhibition was measured by comparing the weight of tumors of the treated rat after excision with the weight of tumors excised from rats utilized as a control who were not administrated either Compound A or Compound B.

The compounds of formula I are also useful as medicaments for the topical and systemic therapy of acne, psoriasis and other related dermatological disorders which are characterized by an increased or pathologically altered cornification, as well as inflammatory and allergic dermatological conditions. They can also be used to treat disorders which are characterized by inflammatory or degenerative alterations of the mucous membranes.

The compounds of formula I can accordingly be used as medicaments; for example, in the form of pharmaceutical preparations which contain them in association with a compatible pharmaceutical carrier. The pharmaceutical preparations serving for systemic application can, for example, be produced by adding the compound of formula I as the active ingredient to non-toxic, inert, solid or liquid carriers which are usual in such preparations. The pharmaceutical preparations can be administered enterally or parenterally. Suitable pharmaceutical preparations for enteral administration are, for example, tablets capsules, dragels, syrups, suspensions, solutions and suppositories. Pharmaceutical preparations in the form of infusion or injection solutions are suitable for parenteral administration.

The pharmaceutical preparations can contain inert or other pharmacodynamically active additives. Tablets or granules, for example, can contain a series of binding agents, fillers, carrier materials or diluents. Liquid preparations can, for example, take the form of a sterile water-miscible solution. Besides the polyene compounds of formula I, capsules can additionally contain a filling material or thickening agent. Furthermore, flavor-improving additives as well as the substances usually used as preserving, stabilizing, moisture-retaining or emulsifying agents, salts for varying the osmotic pressure, buffers and other additives can be present.

The carrier materials and diluents mentioned hereinbefore can be organic or inorganic substances; for example, water, gelatin, lactose, starches, magnesium stearate, talcum, gum arabic, polyalkyleneglycols and the like. It is, of course, a prerequisite that all adjuvants used in the production of the pharmaceutical preparations are non-toxic.

For topical administration, the polyene compounds of formula I are expediently made up in the form of ointments, tinctures, creams, solutions, lotions, sprays, suspension and the like. Ointments and creams, as well as solutions, are preferred. These pharmaceutical preparations intended for topical administration can be produced by mixing the polyene compounds as the active ingredient with non-toxic, inert solid or liquid carriers suitable for topical administration which are usual per se in such preparations or liquid carriers suitable for topical administration which are usual per se in such preparations.

Expedient for topical administration are ca 0.01% to ca 0.3% (preferably 0.02% to 0.1%) solutions as well as ca 0.05% to ca 5% (preferably ca 0.1% to ca 2.0%) ointments or creams.

An antioxidant (e.g. tocopherol, N-methyl-γ-tocopheramine, butylated hydroxyanisole or butylated hydroxytoluene can optionally be added to the pharmaceutical preparations.

In the practice of the present invention, the preferred pharmaceutically acceptable salts of the aforementioned vitamin A acid active compounds are the ammonium, alkali, or alkaline earth metal salts. Especially preferred among the alkali metal salts is the sodium salts as well as the alkaline earth metal salts such as calcium or the ammonium salts or substituted ammonium salts such as mono-, di-, or tri-alkyl ammonium salts.

In accordance with the present invention, a method for the therapeutic treatment of carcinomas, particularly of the skin, gastrointestinal tract, mammary, bladder, respiratory tract or genito-urinary tract is effected through the systemic administration of the compound of formula I or pharmaceutically acceptable salts thereof.

In accordance with the present invention, the compound of formula I can be systemically administered to those susceptible to certain carcinomas of the skin, mammary, bladder, gastrointestinal, respiratory or genito-urinary tract. Certain of the carcinomas to be prevented in accordance with the present invention frequently pass through a definite premalignant stage which can be diagnosed as such. It is a statistical fact that 20 to 30% of such premalignant conditions develop into carcinomas. Each such premalignant condition, however, has a propensity to mature into a cancerous condition if allowed to remain untreated. In these instances, the premalignant stage may be treated systemically to prevent development of a carcinoma therefrom. In other instances, even though a definite premalignant condition cannot be positively diagnosed, the individual who may be susceptible to the carcinomas is maintained on a regimen of the compositions which according to the present invention contain as the active ingredient the compound of formula I.

The terminology "carcinomas" utilized with regard to the prophylactic methods of the present invention encompasses carcinomas affecting epithelial cells of diverse parts of the body, e.g. stratified squamous epithelial cells of the skin and mucous membranes, columnar epithelial cells of the intestinal tract, ciliated epithelial cells of the genitalia and parts of the respiratory tract, such as the nasal passages and pseudostratified epithelial cells of the trachea and bronchi. As recognized by the oncologist, carcinomas affecting these cells include those of the epithelium of the skin, tongue, bladder, breast, pharynx, larynx, bronchus, esophagus, stomach, large bowel, bladder, cervix and vulva and the like.

The daily dosage of the compound of formula I in accordance with the present invention will vary with the needs of the patient, particularly in those instances where a definite premalignant condition has been diagnosed. Generally, a daily dose by enteral or parenteral administration of from about 0.05 mg. to about 3.0 mg. per kg. of body weight of the pateint is utilized. More preferably, a dosage of from about 0.1 mg. to about 1.0 mg. per kg. is utilized. This dosage may be administered in any suitable dosage schedule according to the desires of the clinician in view of the requirements of the patient, the existence of a premalignant condition and other factors such as age of the patient and the like.

The compounds of this invention are effective antitumor screening agents as seen from the administration of Compounds A and B to female rats to preclude the growth of chondrosarcoma. In this test, several small pieces of the chondrosarcoma are implanted subcutaneously in the right inguinal region of 40-50 g rats using a trocar. After 30-40 days, groups of 8 animals are randomly formed and treatment begun by the intraperitoneal (i.p.) daily 5 times per week. Treatment is continued for 4 weeks and then the animals are sacrificed and their tumors excised and weighed.

The inhibition of tumor growth is calculated as $(C-T)/C \times 100\%$ where C and T are the mean tumor weights for the control and treated animals respectively. The results are expressed as % inhibition of tumor growth. If the observed inhibition is 50% or greater, activity is reported as being effective. In the inhibition is less than 50%, inactivity is reported. The results are given in the following table:

| | Inhibition of Chondrosarcoma Growth | | | |
|---|---|---|---|---|
| | Dose | % | Body Weight Change | |
| Compound | (mg/kg/day)* | Inhibition | Treated | Controls |
| A | 20 | 95 | +31 | +34 |
| B | 20 | 94 | +30 | +34 |
|   | 10 | 86 | +22 | +29 |
|   | 5 | 41 | +31 | +29 |

*Animals treated daily, intraperitoneally, Mon-Fri. for 4 weeks.

The toxicity of the compounds of formula I is determined from the toxic hypervitaminosis-A syndrome. The compounds of formula I-A are relatively non-toxic as measured by this syndrome which makes them effective as tumor inhibiting agents and for treating premalignant or malignant conditions in mammals through the internal administration of the compound of formula I either p.o., i.v., i.p. etc.

The toxic hypervitaminosis-A syndrome is calculated by a method explained in "Europ. J. Cancer", Vol. 10 (1974) pp. 731–733. More specifically, the vitamin A hypervitaminosis test is carried out on mice weighing 25–27 g. which over a 14 day period receive 10 i.p. injections of the test substance suspended in arachis oil. The following symptoms are evaluated using a scale from 0 to 4:

| Grade | 0 | 1 | 2 | 3 | 4 |
|---|---|---|---|---|---|
| Loss of weight | <1g. | 1-3g. | 4-6g. | 7-9g. | ≧10g. |
| Skin desquamation | none | slight | moderate | severe | very severe |
| Loss of hair | none | slight | moderate | severe | very severe |
| Bone fractures of extremities (number, macroscopic observation) | 0 | 1 | 2 | 3 | >4 |

Hypervitaminosis-A is defined as that condition of the animals wherein the addition of all the symptom grades yields at least a value of 3. The lowest daily dose able to cause hypervitaminosis-A in the 14-day study is recorded. Compound A produced hypervitaminosis-A by this study at dose of over 100 mg/kg per day and Compound B produced hypervitaminosis-A by this study at a dose of over 200 mg/kg per day.

The tumor inhibiting activity of the compounds of formula I was demonstrated by systemic treatment of papillomas induced by the dimethyl-benzanthracene-croton oil method. In this method, Swiss Albino mice were painted twice, 15 days apart, on a 5 cm² area of their back with 150γ dimethylbenzanthracene (hereinafter DMBA) dissolved in 0.2 ml of acetone. Three weeks after the second painting with DMBA, the same areas were painted with 0.5 mg of croton oil dissolved in 0.2 ml acetone bi-weekly for a period of from three to four months until papillomas appeared. When the papillomas, which were mostly multiple papillomas, had grown to a diameter of approximately 4 mm., the therapeutic treatment was initiated. Groups of four mice were given a dose of a test compound once a week for four weeks. Administration was both per os and intraperitoneal on different groups. On the first and fifteenth day of therapy, the mean radius of the papillomas were measured. The change of mean papilloma volume from day one to day fifteen was determined and expressed as a percent change of the volumes of day one. A control group received no medication. The results of this test are set forth below.

| Compound | Dose | % Regression |
|---|---|---|
| Compound B | 200mg/kg per week | 34% regression |
|  | 100mg/kg per week | 28% regression |

The following examples are given as illustration of the invention:

EXAMPLE 1

(E,E,E,E)-9-(2,6,6-Trimethyl-3-oxo-1-cyclohexen-1-yl)-3,7-dimethyl-2,4,6,8-nonatetraenoic Acid E(5[2,2,5-trimethyl-4-oxo-1-cyclohexenyl]-3-methyl-2,4-pentadiene)triphenyl phosphonium bromide (224 g) and ethyl-β-formylcrotonate (52 g) were dissolved in dichloromethane (1000 ml) and cooled to −10° C. Over a period of 25 min., a solution of sodium methoxide in methanol (3.5 M; 121 ml) was added and the resulting mixture was then stirred for a further ½ hours at 0°.

Acetic acid (10 ml) followed by water (300 ml) was then added and the solvents were removed in vacuo (40° 20–30 ml) was added, the triphenylphosphine oxide was filtered off and the hexane extract was then washed with aqueous methanol (250 ml; 70% MeOH (H₂O)).

The hexane extracts were then concentrated to dryness to yield the ester, 9-(2,2,5-trimethyl-4-oxo-1-cyclohexenyl)3,7-dimethyl-2,4,6,8-nonatetraenoic acid ethyl ester.

The above ester was hydrolized by dissolving this ester in a mixture of methanol (600 ml) containing potassium hydroxide (75 g) and water (100 ml) and heated at reflux for 45 min. The cold reaction mixture was then treated with ice water (1000 ml) acetic acid (100 ml) and the solids were isolated by extraction with dichloromethane (3×750 ml). Removal of the solvents and crystallisation of the residue from ethylacetate, gave (E,E,E,E)-9-(2,6,6-trimethyl-3-oxo-1-cyclohexen-1-yl)-3,7-dimethyl-2,4,6,8-nonatetraenoic acid (35.9 g) m.p. 184–187°.

EXAMPLE 2

(E,E,E,E)-9-(2,6,6-trimethyl-3-hydroxy-1-cyclohexen-1-yl)-3,7-dimethyl-2,4,6,8-nonatetraenoic acid A solution of the (E,E,E,E)-9-(2,6,6-trimethyl-4-oxo-1-cyclohexenyl)-3,7-dimethyl-2,4,6,8-nonatetraenoic acid (1.5 g) in ethanol (25 ml) was cooled to 5° in an icebath and then treated with sodium borohydride (200 mg) and stirred at room temperature for 30 min.

Acetic acid was then added and the solvents were concentrated in vacuo and the residue was extracted with dichloromethane. Removal of the organic solvents and crystallization of the residue from ethylacetate gave pure (E,E,E,E)-9(2,2,5-trimethyl-3-hydroxy-1-cyclohexen-1-yl)-3,7-dimethyl-2,4,6,8-nonatetraenoic acid (lg), m.p 181°–183°. A further crop of crystals was obtained from the mother liquors (150 mg) m.p.. 178°–182°.

EXAMPLE 3

Dragees were prepared in accordance with the art of pharmaceutical compounding from the following ingredients:

| Ingredient | Weight/Degree |
|---|---|
| (E,E,E,E)-9-(2,2,5-trimethyl-4-oxo-1-cyclohexenyl)-3,7-dimethyl-2,4,6,8-nonatetraenoic acid | 16.0 mg. |
| Lactose | 40.0 mg. |
| Corn Starch | 40.0 mg. |
| Talc | 3.5 mg. |
| Stearic acid | 0.5 mg. |
| Coating Composition | 120.0 mg. |
| Total Weight | 220.0 mg. |

EXAMPLE 4

Hard gelatin capsules were filled with the following composition:

| Ingredient | Weight/Capsule |
|---|---|
| (E,E,E,E)-9-(2,6,6-trimethyl-3-oxo-1-cyclohexen-1-yl)-3,7-dimethyl-2,4,6,8-nonatetraenoic acid | 20.0 mg. |
| Talc | 8.0 mg. |
| Lactose | 152.0 mg. |
| Total Weight | 180.0 mg. |

EXAMPLE 5

Soft gelatin capsules were filled with the following composition:

| Ingredient | Weight/Capsule |
|---|---|
| (E,E,E,E)-9-(2,6,6-trimethyl-3-oxo-1-cyclohexen-1-yl)-3,7-dimethyl-2,4,6,8-nonatetraenoic acid | 20.0 mg. |
| Wax Mixture | 51.5 mg. |
| Vegetable Oil | 103.0 mg. |
| Sequestrin[1] | 0.5 mg. |
| Total Weight | 175.0 mg. |

[1] Complexing agent: salt of ethylenediaminetetraacetic acid.

EXAMPLE 6

Dragees were prepared in accordance with the art of pharmaceutical compounding from the following ingredients:

| Ingredient | Weight/Dragee |
|---|---|
| (E,E,E,E)-9(2,6,6-trimethyl-3-hydroxy-1-cyclohexen-1-yl)-3,7-dimethyl-2,4,6,8-nonatetraenoic acid | 16.0 mg. |
| Lactose | 40.0 mg. |
| Corn Starch | 40.0 mg. |
| Talc | 3.5 mg. |
| Stearic Acid | 0.5 mg. |
| Coating Composition | 120.0 mg. |
| Total Weight | 220.0 mg. |

EXAMPLE 7

Hard gelatin capsules were filled with the following composition:

| Ingredient | Weight/Capsule |
|---|---|
| (E,E,E,E)-9(2,6,6-trimethyl-3-hydroxy-1-cyclohexen-1-yl)-3,7-dimethyl-2,4,6,8-nonatetraenoic acid | 20.0 mg. |
| Talc | 8.0 mg. |
| Lactose | 152.0 mg. |
| Total weight | 180.0 mg. |

EXAMPLE 8

Soft gelatin capsules were filled with the following composition:

| Ingredient | Weight/Capsule |
|---|---|
| (E,E,E,E)-9(2,6,6-trimethyl-3-hydroxy-1-cyclohexen-1-yl)-3,7-dimethyl-2,4,6,8-nonatetraenoic acid | 20.0 mg. |
| Wax Mixture | 51.5 mg. |
| Vegetable Oil | 103.0 mg. |
| Sequestrin[1] | 0.5 mg. |
| Total Weight | 175.0 mg. |

[1] Complexing agent: sodium salt of ethylenediaminetetraacetic acid.

We claim:
1. The compound 9(2,6,6-trimethyl-3-hydroxy-1-cyclohexenyl)-3,7-dimethyl-2,4,6,8-nonatetraenoic acid.

* * * * *